United States Patent [19]

Duruz

[11] Patent Number: 4,683,037

[45] Date of Patent: Jul. 28, 1987

[54] DIMENSIONALLY STABLE ANODE FOR MOLTEN SALT ELECTROWINNING AND METHOD OF ELECTROLYSIS

[75] Inventor: J. J. Duruz, Geneva, Switzerland

[73] Assignee: Eltech Systems Corporation, Boca Raton, Fla.

[21] Appl. No.: 864,057

[22] Filed: May 16, 1986

[30] Foreign Application Priority Data

May 17, 1985 [EP] European Pat. Off. ........ 85810235.3

[51] Int. Cl.$^4$ .......................... C25C 7/02; C25C 3/12
[52] U.S. Cl. .................................. 204/64 R; 204/67; 204/290 R; 427/123; 427/126.1; 252/521
[58] Field of Search ................ 204/64, 67, 39, 290 R; 427/123, 126.1, 126.2; 252/521

[56] References Cited

U.S. PATENT DOCUMENTS 4,192,724 3/1980 Minami et al. ........................ 204/67
4,233,148 11/1980 Ramsey et al. ..................... 204/291
4,438,214 3/1984 Masuyama .......................... 252/521

FOREIGN PATENT DOCUMENTS 0114085 7/1984 European Pat. Off. .......... 204/64 R

Primary Examiner—John F. Niebling
Attorney, Agent, or Firm—John J. Freer

[57] ABSTRACT

The morphology of a coating of Ce oxyfluoride on a conductive substrate is improved by addition of yttrium, lanthanum, praseodymium and/or other rare earth metals. Whereas the pure Ce-oxycompound coating shows cracks which frequently extend throughout the entire thickness of the coating, thus exposing finite portions of the substrate to eventual corrosive attack from the environment, the improved coating including the above doping element(s) comprises a substantially impervious structure. Coatings of this nature may be employed with non-consumable anodes in molten aluminum electrowinning cells or as chemical sensors, corrosion protection and other applications.

14 Claims, 4 Drawing Figures

DIMENSIONALLY STABLE ANODE FOR MOLTEN SALT ELECTROWINNING AND METHOD OF ELECTROLYSIS

FIELD OF INVENTION

The invention relates to a coating for conductive substrates, comprising an oxyfluoride of cerium providing enhanced resistivity against reducing as well as oxidizing environments up to temperatures of 1000° C. and higher.

The invention further relates to a method of manufacturing said coating.

Coatings according to the invention may be used to form non-consumable anode components for electrowinning of metals from molten salts, but there are also other possible applications, e.g. sensors for the chemical composition of fluids, such as oxygen sensors for gasses or liquid metals. Further the coatings may be used for corrosion protection at high temperature, and generally for applications where electronic and/or ionic conductivity combined with chemical stability at high temperatures are desirable. Enhanced chemical stability at high temperatures is desired e.g. for protective coatings of heat exchangers exposed to corrosive environments.

BACKGROUND OF INVENTION

The European Patent Application No. 0 114 085 published on July 25, 1984 discloses a dimensionally stable anode for an aluminum production cell comprising a conductive substrate of a ceramic, a metal or other materials which is coated with a layer of cerium oxycompound. The anode is essentially stable under conditions found in an aluminum production cell, provided that a sufficient content of cerium is maintained in the electrolyte.

The anode as described in the above European patent application performs well in respect of dimensional stability, however, contamination of the produced aluminum by substrate components may occur under certain circumstances. As shown by microphotographs, the cerium containing coating can be comprised of a non-homogeneous and non-continuous structure leaving small interstices between coated areas, which provide access of the electrolyte to the substrate. In such cases, the electrolyte may corrode the substrate leading to a limited but undesired contamination of the aluminum by substrate components.

It had also been speculated that the above described coating may consist of other rare earth metals such as praseodymium, samarium, europium, terbium, thulium or ytterbium in a suitable concentration. However these elements are not easy to be coated under the conditions provided in the above publication which does not contain any instructions as to how these elements may be coated onto the substrate, nor in which ranges of concentration. Further, it does not contain any suggestion as to a possible beneficial effect of these elements.

The French patent application No. 2 407 277 discloses a method of electrolyzing chlorides of e.g. magnesium, sodium, calcium or aluminum in electrolytes having temperatures between 500°-800° C. using an anode comprising a substrate and a coating of an oxide of a noble metal, whereby a certain concentration of an oxide or oxychloride of a metal which is more basic than the metal produced is maintained in the bath. Thus, by increasing the basicity of the bath the solubility of the anode coating is reduced.

This method provides better stability of the anode coating by the addition of melt additives, however, these additions relate to the stabilization of the coating rather than to the improvement of the coating morphology and does therefore not contribute to the improvement of the substrate-protection which is not always completely satisfactory in the case of a pure cerium oxycompound coating being one of the hereunder defined objects of the present invention. The substrate itself which is essentially protected by the coating and only subject to corrosion at finite deficient locations thereof may not simply be protected against corrosion by modifying the basicity of the bath as described in the French patent, since the anode substrate according to the present invention is unstable in a fluoride bath at e.g. 960° C. and needs therefore to be completely shielded therefrom. A mere modification of the basicity would not improve the stability of the substrate as it does with a coating of an oxide of a noble metal which is essentially stable in the bath per se.

OBJECTS OF THE INVENTION

It is one object of the invention to provide a remedy for the above described contamination problem.

It is another object of the invention to provide a dimensionally stable anode for electrowinning of a metal from a molten salt electrolyte containing an oxide of said metal, the anode having a coating which completely inhibits the access of the electrolyte to the substrate.

It is a further object of the invention to provide a method of producing aluminum or other metals using a dimensionally stable anode comprising a coating wherein the formation of crevices and other deficiencies which allow access of the electrolyte to the substrate is elimnated.

It is a further object of the invention to provide a simple technique for inhibiting the contamination of the aluminum by substrate components by a method which is simple to apply, which is inexpensive and which does not require any modifications of the anode itself or of the cell.

Finally, it is an object of the invention to provide a coating with improved properties for general applications where at least one or a combination of the following properties—electronic and ionic conductivity and chemical stability against oxidizing as well as reducing environments at high and low temperatures—are desirable.

SUMMARY OF THE INVENTION

The above and other objects are met by a coating as mentioned under the heading "FIELD OF INVENTION", characterized by the coating further comprising at least one doping element selected from the group consisting of yttrium, lanthanum, praseodymium and other rare earth metals, the concentration of the doping element(s) in the coating being less than 10 w % in respect of Ce, the coating having a continuous coherent structure thereby providing a substantially impervious layer on the substrate.

Coatings according to the invention may comprise oxyfluorides of cerium and the coping element(s), whereby the concentration of the doping element(s) is between 0.1–5 w % of the cerium content.

The above coating may be deposited onto a substrate being a metal, an alloy, a ceramic material, a cermet and/or carbon. A particularly preferred substrate is $SnO_2$, or $SnO_2$ based materials.

The coating may be produced by deposition of the constituents thereof onto the substrate immersed in an electrolyte containing said constituents in dissolved state.

The coating according to the invention may serve in conjunction with a suitable substrate as an anode for electrowinning of metals by molten salt electrolysis, in particular for the production of aluminum from alumina dissolved in molten cryolite.

However, other uses of such coatings are intended and covered by the scope of the invention. Such other possible uses and applications of the coating were already mentioned in the preamble of this specification and comprise chemical sensors, corrosion protection, and chemically stable coatings for high and low temperatures.

In accordance with the invention a method of producing a coating as described above is characterized by adding sufficient amounts of compounds of cerium and at least one doping element selected from the group consisting of yttrium, lanthanum, praseodymium and other rare earth metals to the electrolyte and passing electrical current therethrough, whereby said coating and substrate are kept under anodic polarization.

Good results for the morphology of the coating have been achieved with concentrations of the doping element(s) in respect to cerium ranging from approximately 1:1 in example 2 to approximately 4,7:1 in example 3. The cerium concentration in the electrolyte was 1.2 w % in both cases. It should be noted that the concentration of the doping elements in the deposit does not significantly change with variations of their concentration in the electrolyte above a certain level, since a maximum concentration of the doping element in the coating is expected which corresponds to the thermodynamic solubility of the doping elements in the Ce oxyfluoride crystal lattice. On the other hand, however, the above values for the concentration of the doping elements may not be substantially decreased without affecting the coating composition and morphology. According to the differences of the doping elements and parameters of the coating process the concentration of the doping elements in respect to cerium may vary from 0.1:1 to 100:1.

It is convenient for the bath chemistry if the compounds of the doping elements are oxides and/or fluorides thereof.

Further features of the invention are the employment of the above described method of manufacture for the production of non-consumable anodes for metal electrowinning from its oxide dissolved in a molten salt electrolyte such as the production of aluminum by electrolysis of alumina dissolved in molten cryolite, which method comprises adding to the electrolyte prior to or during a preliminary period under special electrolysis operating conditions or during normal electrolysis a sufficient amount of compounds of cerium and at least one doping element selected from the group comprising yttrium, lanthanum, praseodymium and other rare earth metals. Continuing operation of the anode for producing metal may be assured by maintaining sufficient concentrations of cerium and, if necessary, the doping element throughout normal electrolysis.

The initial production of the coating on the substrate may be carried out outside a molten salt electrowinning cell prior to the use of the anode in said cell, or during preliminary or normal electrolysis operating conditions within said electrowinning cell.

The choice and concentration of the doping elements from the mentioned group comprising yttrium, lanthanum, praseodymium and other rare earth metals may be carried out according to the intended use of the coating, and will generally be governed by considerations of how the particular element influences the morphological, chemical and electrical properties of the coating. Some of the mentioned doping elements such as yttrium create enhanced ionic conductivity, which may be of interest for the sensor application, however, for its use as coating for dimensionally stable aluminum electrowinning anodes the electronic conductivity should prevail. Since the raise of the ionic conductivity with the addition of most doping elements of the above group is dependent on the concentration thereof, this concentration should not be too high in cases where the electronic conductivity is the desired form of conductivity, provided the morphology of the coating is sufficiently improved.

DETAILED DESCRIPTION OF THE INVENTION

Figure 1:

The invention is now described in view of its application as a coating for dimensionally stable anodes for electrowinning of metals by molten salt electrolysis.

The dimensionally stable anodes over which the anodes of the present invention are an improvement are described in the European Patent Application No. 0 114 085, this document being referred to such as fully incorporated herein.

As mentioned under the heading "BACKGROUND ART" the known anode coating comprised of cerium oxyfluoride lead to a contamination of the aluminum by corrosion of the substrate to which the electrolyte finds limited access by small imperfections of the cerium-coating.

The present invention is based on the finding that the addition of small amounts of doping elements which coprecipitate with the cerium on the anode substrate modifies the coating morphology in such beneficial manner that the coating is developed with a continuous coherent structure, thereby providing a substantially impervious layer on the substrate, which completely sheathes the latter and avoids thereby any access of electrolyte.

The cerium based coating including these doping elements selected from yttrium, lanthanum, paseodymium and other rare earth metals may be prefabricated outside the electrolysis cell or within the cell during preliminary operating conditions, or it may be established during normal operation by immersing an uncoated substrate into the electrolyte whereby controlled amounts of compounds such as oxides and/or fluorides of cerium and the doping elements are added to the electrolyte and maintained at a certain concentration.

The mentioned doping elements and their respective oxyfluorides do not precipitate on anode substrates such as $SnO_2$ other than together with the cerium compounds and even in the presence of cerium the doping elements precipitate onto the anode substrate in a rate which is substantially lower than it could be expected according to their concentration in respect of the cerium content in the electrolyte. The doping elements or their oxyfluorides are completely dissolved in the solid cerium oxyfluoride phase of the coating. It may therefore be possible that the content of the doping elements at least in an inner region thereof be kept at its initial level, thus maintaining the imperviousness in this region even without further doping elements being added to the electrolyte, whereby only the concentration of Ce needs to be maintained. Alternatively, in order to maintain the concentration of cerium and the doping elements in the molten salt electrolyte, Misch metal oxides may be added thereto which contain a major amount of cerium oxide and minor amounts of other rare earth metal—as well as ytrrium—oxides. A suitable composition among a variety of different natural ores containing Misch metal oxides may be chosen according to the final use of the coating.

The coating according to the invention is comprised of an oxyfluoride material which is extremely resistant to strong reducing as well as oxidizing environments such as found in a Hall-Heroult cell. The material is resistant to oxygen which is released in substantial amounts from the melt in the case of non-carbon anodes, and against fluorine or fluorides being present from the cryolite. The coating is resistant against these gasses since it is already comprised of an oxyfluoride compound which is inert against further attack by fluorine and oxygen. However, the cryolite in such cells contains a certain concentration of dissolved metallic aluminum which is highly reducing in particular at the temperatures involved. The above coating, however, is neither reduced by liquid aluminum in bulk or dissolved in cryolite, since the oxides of Ce and the other doping elements are more stable than aluminum oxide.

These very slowly dissolving anode coatings may be operated under constant conditions, whereby an equilibrium between the dissolution rate of the coating in the electrolyte and the deposition rate of the dissolved constituents is maintained, or the operation conditions may be controlled intermittently, whereby the anode is operated until a minimum coating thickness representing a safety limit is achieved, beyond which contamination of the bath and the product metal by corrosion of the substrate may not be avoided. Alternative methods may then be provided which comprise re-growing the coating by adding to the electrolyte the necessary compounds as mentioned above or withdrawing the spent anodes to put in new ones, whereby the used anodes may be recoated outside the cells for further use.

The choice of a particular doping element depends—as already mentioned—on the intended application of the coating. In the case of the use of these coatings for aluminum electrowinning anodes it should be considered that oxyfluorides of the metals in question have a certain electronic but also ionic conductivity as already mentioned before. While electronic conductivity is the preferred form, the ionic one leads under particular conditions to the formation of a sub-layer between the substrate and the coating, this sub-layer being depleted of oxygen and comprising substantially pure fluorides of Ce and the doping elements. The latter should therefore not substantially enhance the ionic conductivity over that of Ce oxyfluoride. Praseodymium, yttrium, lanthanum and some others are in this respect acceptable candidates. While lanthanum would be acceptable in this respect, its electrowinning potential allows in the case of its use in an aluminum electrowinning cell coprecipitation with the aluminum produced, so that the contamination of the product metal is unacceptable. However, the employment of doping elements which are not suitable for aluminum electrowinning anodes may be envisaged for other applications.

The invention is further described by three examples and microphotos demonstrating the improvement of the coating morphology by addition of the above described doping elements.

For this purpose FIG. 1 shows a coating achieved by immersion of a $SnO_2$ substrate into a bath as described in the examples but without any doping element, only with 1.2% Ce. It is apparent that the coating 1 covers the substrate 2 in a non-satisfactory manner. Large crevices 3 and voids 4 are visible in the coating which cause access of the electrolyte to the substrate which is not resistant to the latter. In addition to this large imperfections very fine microcracks 5 are visible which, however, are due to the thermal shock to which all samples were subjected when they were removed from the hot test cell. These microcracks which are also visible in the other Figures do not occur under normal operation.

Figure 2:
Figure 3:
Figure 4:

FIGS. 2 to 4 show coatings which were made according to the examples including the doping additives. As compared to FIG. 1, the coatings 1 in FIGS. 2, 3 and 4 are substantially improved in respect of their sealing effect for the substrate, i.e. their imperviousness. All large imperfections have disappeared, only the above mentioned microcracks which are due to the sample preparation are still visible. It is perceivable that such improved anode coatings are highly beneficial in order to reduce corrosion of the anode substrate by the electrolyte and the contamination of the metal produced.

EXAMPLES

EXAMPLE 1

To 340 g electrolyte comprising 90 w % cryolite and 10 W % $Al_2O_3$ were added 4 g $CeF_3$ and 17 g $Y_2O_3$. Electrolysis was carried out for 30 hours at 960° C. with an anodic current density of approx. 0.2A/cm². After the electrolysis, the anode was found to be coated with a 0.44 mm thick layer comprising approx. 98 w % Ce-oxyfluoride and approx. 2 w % Y-oxyfluoride. The microphoto (FIG. 2) shows a continuous coherent coating which is free from the afore mentioned crevices and holes, whereby no substrate portions are exposed to the electrolyte. The microcracks 5 do not have any influence on the coating performance, since they are due to the sample preparation and would not occur in normal operation.

EXAMPLE 2

To 340 g electrolyte comprising 90 w % cryolite and 10 w % $Al_2O_3$ were added 4 g $CeF_3$ and 3.5 g $Pr_6O_{11}$. Electrolysis was carried out for 30 hours at 960° C. with an anodic current density of approx. 0.2A/cm². After the electrolysis the anode was found to be coated with a 0.37 mm thick layer comprising approx. 97 w % Ce-oxyfluoride and approx. 3 w % Pr-oxyfluoride. The microphoto (FIG. 3) shows a continuous coherent coating which is free from the afore mentioned crevices and holes, whereby no substrate portions are exposed to the electrolyte.

EXAMPLE 3

To 340 g electrolyte comprising 90 w % cryolite and 10 W % $Al_2O_3$ were added 4 g $CeF_3$ and 17 g $LaF_3$.

Electrolysis was carried out for 30 hours at 960° C. with an anodic current density of approx. 0.2A/cm$^2$. After the electrolysis the anode was found to be coated with a 0.44 mm thick layer comprising approx. 99 w % Ce-oxyfluoride and approx. 1 w % La-oxyfluoride. The microphoto (FIG. 4) shows a continuous coherent coating which is free from the afore mentioned crevices and holes, whereby no substrate portions are exposed to the electrolyte.

I claim:

1. In an electrowinning cell having a substrate with a coating comprising an oxyfluoride of cerium providing enhanced resistivity against reducing as well as oxidizing cell environments up to temperatures of 1000° C. and higher, characterized by the coating further comprising at least one doping compound of an element selected from the group consisting of yttrium, lanthanum, praseodymium and other rare earth metals, the concentration of the doping compound(s) in the coating being less than 10 w % of the cerium constituents in the coating, the coating having a continuous coherent structure thereby providing a substantially impervious layer on the substrate.

2. The coated substrate of claim 1, characterized by comprising a structure of oxy-fluorides of cerium and the doping compound(s), the concentration of the doping compound(s) being between 0.1-5 w % of the cerium constituents concentration.

3. The coated substrate of claim 1 or 2, characterized by the substrate being one or more of a metal, an alloy, a ceramic material, a cermet, or carbon coated with one or more of the foregoing.

4. The coated substrate of claim 3, characterized by the substrate comprising SnO$_2$.

5. The coating of claim 1, characterized by being produced by deposition of all of the constituents thereof onto the substrate immersed in a molten salt electrolyte containing coating constituent precursors in dissolved state.

6. The coating of claim 5, characterized in the electrolyte being cryolite.

7. A dimensionally stable anode for electrowinning of a metal from an oxide thereof dissolved in a molten salt electrolyte, the anode comprising an electroconductive substrate and a coating according to claim 1.

8. The method of claim 13, characterized by producing aluminum.

9. A method of producing a continuous, coherent and conductive coating on a conductive substrate, said coating having enhanced resistivity against reducing as well as oxidizing environments up to temperatures of 1000° C. and more, said method being characterized by adding to a cell electrolyte compounds of cerium and at least one doping compound precursor substance containing one or more metals selected from the group consisting of yttrium, lanthanum, praseodymium and other rare earth metals, and passing electrical current therethrough with said coating and substrate under anodic polarization.

10. The method of claim 9, characterized by the concentration of the doping compound precursor substances in the electrolyte being in the range of 0.1 to 100 times the concentration of cerium compounds.

11. The method of claim 9, characterized by precursor substances of the doping compounds being one or more of metal oxides or fluorides.

12. An anode for electrowinning of a metal from an oxide dissolved in a molten electrolyte, the anode comprising a conductive substrate and a coating produced by the method according to claim 9.

13. A method of producing a metal by electrolysis of a compound of said metal dissolved in a molten salt electrolyte using a coated anode according to claim 7, characterized by adding to the electrolyte a cerium compound precursor substance and a doping compound precursor substance containing at least one metal selected from the group consisting of yttrium, lanthanum, praseodymium and other rare earth metals, and maintaining at least the cerium compound precursor substance in the electrolyte during electrolysis.

14. The method of claim 13, characterized in producing the coating on the anode either outside a molten salt electrowinning cell, prior to the use of the anode in said cell, or in a molten salt electrowinning cell during electrolysis.

* * * * *